United States Patent [19]

Apple et al.

[11] 4,053,460
[45] Oct. 11, 1977

[54] AZETOMICINS

[75] Inventors: Martin A. Apple, Daly City, Calif.; Joseph V. Formica, Richmond, Va.

[73] Assignee: The Regents of the University of California, Berkeley, Calif.

[21] Appl. No.: 605,425

[22] Filed: Aug. 18, 1975

[51] Int. Cl.$^2$ .................. C07C 103/52; A61K 37/00
[52] U.S. Cl. ........................ 260/112.5 R; 195/29; 195/51 R; 424/177
[58] Field of Search ............... 260/112.5 R; 424/177

[56] References Cited

PUBLICATIONS

Hollstein: Chem. Rev. 75, 625–652 (1974).

Primary Examiner—Delbert R. Phillips
Attorney, Agent, or Firm—Phillips, Moore, Weissenberger, Lempio & Majestic

[57] ABSTRACT

Modified actinomycin compounds that incorporate azetidine in the polypeptide component of the actinomycin molecule are disclosed. These compounds are called Azetomicins and specifically incorporate an azetidine derivative in the 3' peptide position in at least one of the two polypeptides normally present in actinomycins. The Azetomicins are produced by bio-synthetic means from *Streptomyces antibioticus* that are cultured on a medium including azetidine-2 carboxylic acid and derivatives thereof.

6 Claims, No Drawings

AZETOMICINS

BACKGROUND OF THE DISCLOSURE

The invention disclosed herein was made during the performance of work under a research grant from the United States Public Health Service.

Actinomycin drugs have been known since the early 1940's when Waksman and Woodruff isolated and described the first actinomycin. The actinomycins are a group of antibiotics that occur naturally as metabolic products of the growth of *Streptomyces antibioticus* (formerly known as *Actinomyces antibioticus*) and related species, such as *S. chrysomallus*, *S. parvullus*.

The antinomycins are orange to red antibiotics, that are highly toxic to most animal species. However they have found usage in nontoxic dosages principally because of their antineoplastic effects. Several actinomycins, specifically, Actinomycin D (or $C_1$), and $C_3$ are highly effective chemotherapeutics in the treatment of Wilms' tumor, trophoblastic tumors and rhabdomyosarcoma. Recently, further successes have been achieved by utilizing the actinomycins in combination with other drugs against various types of neoplastic disease.

In addition, it has been determined that the actinomycin molecule binds to desoxyribonucleic acid (DNA) and thereby interferes with the synthesis of ribonucleic acid (RNA). This phenomenon has also given rise of the use of actinomycins as a tool in the study of molecular and cell biology.

Structural studies have revealed that the actinomycin molecule is a chromopeptide, i.e., the molecule contains a chromophore moiety that is linked to a peptide moiety.

The chromophore has been shown to be 3-amino-1, 8-dimethyl-2-phenoxazone-4, 5-dicarboxylic acid derivative, or:

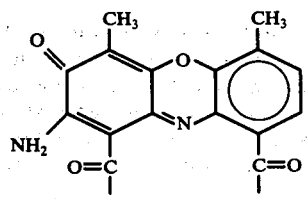

more commonly referred to as "actinocin". The chromophore at its two carboxyl sites in turn carries, as amides, two pentapeptides, whose amino acid sequences may be identical, one with the other, in which case the actinomycin is referred to as an "isoactinomycin"; or, when one pentapeptide differs from the other, as an "antisoactinomycin".

While the peptides may have some differences in their amino acid sequences, the actinomycins invariably have but five amino acid moieties in the peptide chains. In addition the amino acids linked to the 4- and 5-carboxyls by amide bonds are always L-threonine, whose hydroxyl is always lactonized with the carboxyl of the fifth amino acid on the peptide chain. The second amino acid may be D-valine or D-allo-isoleucine, while the third may be L-proline, L-γ-hydroxyproline, L-γ-keto-proline, pipecolic acid (not a naturally occuring actinomycin), or sarcosine. The fourth amino acid is always sarcosine, while the fifth may be L-N-methylvaline or L-N-methylisoleucine. As used herein, reference to the free form of an amino acid, e.g., valine, may also be taken to refer to the peptide form, e.g., valyl, etc. Thus, a typical abbreviated structural representation of an actinomycin (D or $C_1$) is:

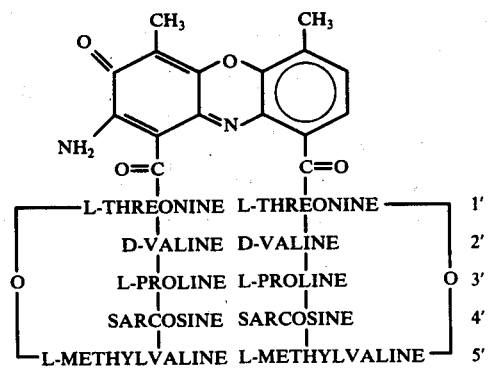

The primed numbers to the right are conventional notations indicating the position of the amino acid on the peptide chain.

Although the amino acids within the peptide substituents may be varied only within narrow limits as noted above, the existence of numerous actinomycins is possible because of the unusual structure. Varying the substituents on the chromophore, and/or on the amino acids in the peptide chain can lead to literally hundreds of actinomycin variations and analogues. A great many such variations have been produced both by biosynthesis and by chemical synthesis so that they can be studied as possible valuable materials for chemotherapy applications. Unfortunately, to date, such variations have shown activies of a low order, or no biological activity at all, with a few exceptions of analogues produced by biosynthesis. Generally, however, the early identified naturally produced actinomycins exhibit the highest activities for biological usage.

BRIEF DESCRIPTION OF THE INVENTION

A new class of actinomycin analogues has been produced and preliminarily tested. The tests indicate that such analogues exhibit excellent biological activity of an order that promises a high probability that this class of actinomycin analogues may be useful in the therapy of human diseases of the neoplastic variety. There is further indication that they may find use as immunosuppressive drugs. These analogues have also exhibited cytotoxic activity against newly fertilized ova, thus suggesting use in contraceptive therapy. In any event the analogues have already shown significant effect against various types of neoplastic diseases in both mice and virus induced neoplastic disease in chickens. Inhibitory activity against the growth of a cross section of Gm+ bacteria has also been shown by these analogues.

Specifically the class of actinomycin analogues of the invention are those analogues wherein azetidine-2-carboxylate and/or its derivatives are substituted for proline normally occupying the 3' position on the peptide moieties attached to actinomycin chromophores. The azetidine substituent may be present in either one or both of the peptide moieties. In an abbreviated representation, such analogues are:

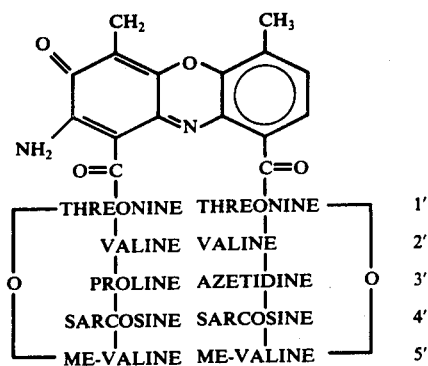
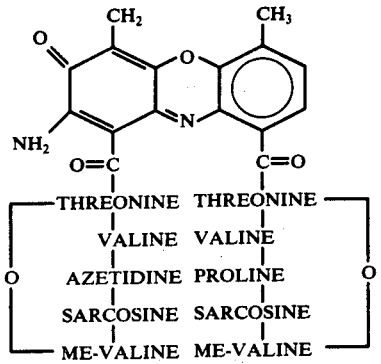

The above analogues are referred to as Azetomicin I, with the I indicating the presence of a single azetidine-carboxylate substituent on the molecule. It will be further noted there are two isomeric Azetomicin I's.

The analogues may further comprise the disubstituted or bis-molecules, for example:

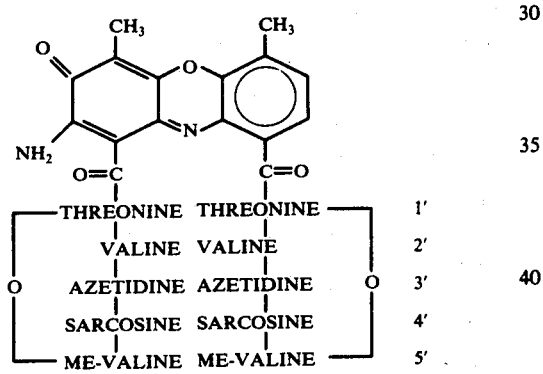

Such analogues are referred to as Azetomicin II.

The Azetomicins are produced biosynthetically by growing *Streptomycetes antibioticus* in a medium that includes the desired azetidine compound. Such a process yields both Azetomicin I and Azetomicin II compounds. The Azetomicins and associated actinomicins are separated, one from the other, by chromatographic techniques.

The Azetomicins show unusually high biological activities when tested against the types of neoplasias used in screening procedures for antinoeplastic drugs.

It is therefore an object of the invention to provide Azetomicins.

It is another object of the invention to provide mono-azetidine-carboxyl substituted Azetomicins.

It is another object of the invention to provide di-azetidine-carboxyl substituted Azetomicins.

It is still another object of the invention to provide a process for producing Azetomicins.

It is another object of the invention to provide Azetomicins exhibiting high biological activities.

Other objects and advantages of the invention will be apparent from the following specification and the claims appended hereto.

DETAILED DESCRIPTION OF THE INVENTION

The compositions of the invention comprise actinomycin analogues wherein the 3' amino acids on the peptide moieties contain azetidine groups. The azetidine groups may appear in either one or both 3' positions since there are two peptide moieties attached to the actinomycin chromophore. If the azetidine group appears in only one 3' position the compound is referred to as Azetomicin I, or if in both 3' positions, as Azetomicin II.

The azetidine substituent group comprises a heterocyclic four-membered ring structure with a carbonyl attached to the carbon in the 2 position as follows:

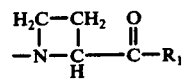

wherein $R_1$ substituent may be any suitable group that facilitates incorporation of azetidine into the peptide chain. It has been found that the simple carboxylic acid group most easily facilitates incorporation of the azetidine into the peptide chain by biosynthesis with *S. antibioticus*. Thus L-azetidine-2-carboxylic acid,

is the preferred starting material in the biosynthesis of Azetomicins.

A number of variations of azetidine-2-carboxylic acid might by utilized to produce Azetomicin analogues. Specifically, substituents, such as halogens, ketones, hydroxyl and methyl groups, etc., may be added to the carbon in the third position on the azet ring thus:

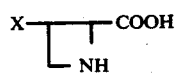

where x is any of the aforestated substituent groups. However Azetomicins already studied and incorporating the unsubstituted azetidine ring exhibit high biological activities.

The formula of Azetomicin I is as follows:

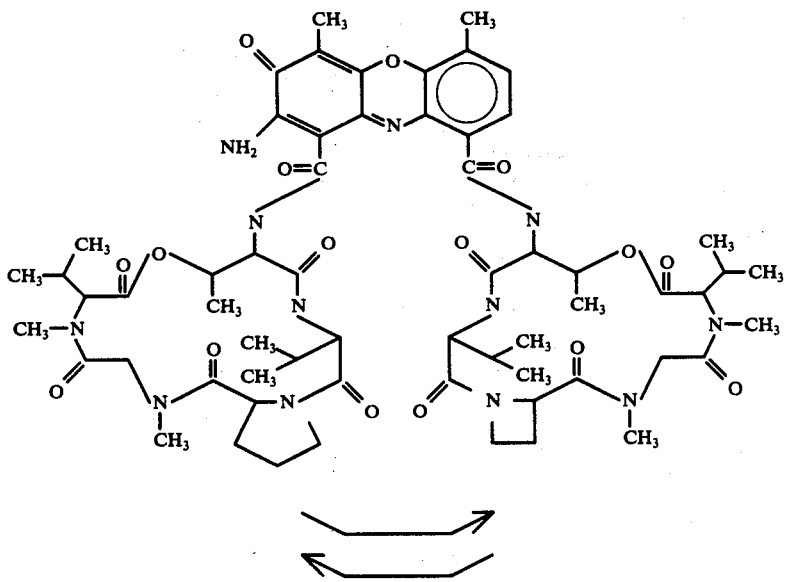

wherein the double arrows indicate that each peptide chain may occur on either side of the chromophore, i.e., there are 2 Azetomicin I isomers. It should be also noticed that proline occupies the 3' position on the corresponding peptide chain. However there are a great number of proline analogues, including, for instance,

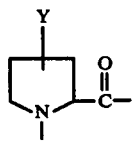

wherein y is a halogen, an hydroxyl, or a ketone, etc.

It has also been found that pipecolic acid may take the place of the proline 3' substituent on the peptide chain. The Pipecolic acid substituent is:

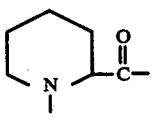

and in the peptide, the carboxyl is connected to the adjacent 4' sarcosine, while the nitrogen is connected to the adjacent 2' valine. There are many pipecolic based variations, as by way of example:

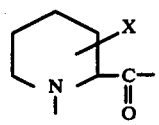

wherein x is a halogen, an hydroxyl, a ketone (=O), a methyl, carboxyl, etc; or:

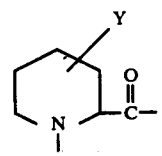

whereby y is a halogen, an hydroxyl, a ketone, or a methyl group, etc.

Further variations in the Azetomicin are possible, such as, for example, elsewhere on the peptide chains. There are 2' amino acid, that is most usually D-valine, may be allo-isoleucine on either one or both peptide chains. Additionally, the chromaphore itself can be varied by substituting heteroatoms for carbons in some ring positions, e.g.:

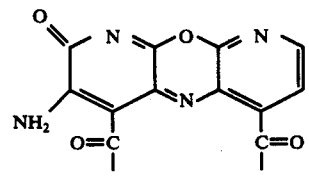

while —NO₂ or —NH₂ may be added on to the 7- carbon; or a halogen may be added on to various position carbons.

The Azetomicin II molecule is identical with the Azetomicin I molecule except that a second azetidine moiety is substituted in place of the 3' proline on the second peptide chain. Azetomicin II is thus anisomeric with respect to the 3' position since both peptides are identical in structure. However, should different amino acids be present in the other peptide positions, then, of course, isomers will exist.

Variations are also possible in the Azetomicin II molecule, in that substituted azetidines may be used; the 2' amino acids may be varied as noted above; and the chromophore itself may have the above indicated substituents added thereto.

In all, there appear to be over 1000 possible variants to the Azetomicin molecules; and anyone, or all, may exhibit biological activities.

The production of Azetomicins can be prepared by chemo-synthetic methods or by biosynthesis utilizing *Streptomyces antibioticus* (or other related species), which is also commonly used in producing the closely related actinomycins. It has been observed that very often the 3'-prolyl moiety appearing in actinomycins can be replaced by an exogenously added amino acid when *S. antibioticus* is actively synthesizing actinomycins. This technique is applicable in the production of Azetomicins.

In brief, *S. antibioticus* is grown on an enzyme-hydrolyzed protein medium to its maximum growth and the culture is then separated from the growth medium by centrifuging or filtering. The collected culture, *S. antibioticus*, is then placed in an actinomycin growth medium to which pure L-azetidine-2 carboxylate (or D,L-azetidine-2-carboxylate) has been added. The *S. antibioticus* is then allowed to produce a mixture of actinomycins and Azetomicins. The actinomycins and Azetomicins are extracted from the growth medium with ethyl acetate and the various compounds are then separated by chromotographic techniques. The individual pure compounds are thus obtained for further use.

More specifically, the following is an example of the production of the Azetomicins:

The initial growth of *S. antibioticus* was developed on Noble agar-beef extract enzyme-hydrolyzed protein medium (A blood-agar medium can also be used). A typical medium was 2.5 gm. N-Z-amine plus 1.0 gm. beef extract plus 100 ml. tap water, adjusted to pH 7.1 and autoclaved 7–15 minutes at 121° C.

The *S. antibioticus* was innoculated into the prepared medium and the culture was incubated for approximately 47 hours, at which time the *S. antibioticus* was harvested at about 15,000 × g. The cell pellet was washed in isotonic saline and thereafter was placed in the Azetomicin production medium which contained 100–250 mc gm/ml L-azetidine-2-carboxylate, L-glutamic acid hydrochloride (2–5 gm/l), D-galactose, D-glucose, $Zn^{++}$, $Fe^{++}$, $Ca^{++}$, and $Mg^{++}$. The medium was buffered to pH 7.2 with potassium phosphate-sodium hydroxide.

The culture medium was then incubated for from 3–6 days at which time production was complete and the medium was a clear yellow color.

The *S. antibioticus* was then separated from the production medium by filtration (it can be re-innoculated into a fresh production medium to produce another batch of Azetomicins without further growth). The *S. antibioticus*-free production medium was then extracted with an equal volume of ethyl acetate, and the ethyl acetate was separated and evaporated to a small volume having a deep orange-red color. To store the Azetomicin-actinomycin product, the acetate ester solution is evaporated to dryness and the resultant powder is redissolved in acetone and stored in the dark under refrigeration.

To separate the Azetomicins, a two phase mixture of the sodium salt of 3-methyl salicylate with ethyl acetate and butyl ether (4:3:1) was prepared and utilized to resolve the mixed Azetomicin-actinomycin product. The solution was then processed on a descending paper chromatograph. The Azetomicin and actinomycin bands separated quite clearly by this method. Column chromatography can also resolve the Azetomicins on a larger scale.

The individual Azetomicin bands were then cut out and the product eluted therefrom with 90% methanol. The Azetomicin-methyl salicylate mixture was dried by evaporating the methanol. The resultant dried product was then dissolved in sodium carbonate solution and then shaken with chloroform in a separatory funnel to transfer the Azetomicin into the chloroform phase. The chloroform extraction was repeated until the chloroform phase was colorless, the chloroform fractions were washed with water and then combined and evaporated to dryness. The resultant pure Azetomicin was redissolved in a minimum amount of acetone for storage.

All chromatographic separations and storage of the resultant products were done in the dark.

The major products of interest were determined to be Azetomicin I and Azetomicin II. They were stable after storage at 0°–25° C in aqueous solution in the pH range of 5–8 for at least 5 days when maintained in the dark.

In the absence of L-azetidine-2-carboxylate in the production medium, the main product contains two 3'-prolyl moieties. Thus the product corresponds to Actinomycin D. In the presence of L-azetidine-2-carboxylate in the production medium additional compounds are produced. In one of these the prolyl-azet ratio is 1:1 and quantitatively there is one less prolyl per molecule. This product corresponds to Azetomicin I. In another product no prolyl moiety is detectable, and there are two azetidinyl-carboxyl moieties per molecule. This product corresponds to Azetomicin II. In both Azetomicin I and II all other analyses are identical to the Actinomycin bis 3'-prolyl compound.

BIOLOGICAL TESTING

Both Azetomicin I and Azetomicin II, produced by the noted biosynthesis method, were tested for biological activities. Since the related actinomycins have shown utility in treatment of neoplastic disease, both Azetomicins were subjected to screening tests devised to reveal promising antineoplastic drugs.

Some samples of Azetomicin I and Azetomicin II were sent to the National Cancer Institute to be tested in the National Screening Center.

One of the most effective preclinical screening devices is a test of the drug agent's ability to produce an increased life span (% ILS) in mice previously infected with well defined types of cancer. The National Cancer Institute has found that drugs which increase the longevity of mice previously implanted with L-1210 leukemia, or P-338 leukemia, or B-16 melanoma by over 50%, i.e., % ILS = 50+%, tend, with a high probability, to be clinically active and useful in man. It has also been found that drugs which increase mouse life span over 100% are far less frequent and tend to be more frequently adapted for clinical use. Out of literally hundreds of thousands of potential agents screened for anticancer activity, only a small handful have the potency to increase the life span of leukemic mice over 200%, and, to date, almost all of them are accepted among the thirty or so clinically useful anticancer drugs; however many such clinically useful anticancer drugs do not show this much activity.

The National Cancer Institute conducted a screening test on samples of both Azetomicin I (3' prolyl, 3' azet) and Azetomicin II (3', 3' azet) as well as on Dactinomycin (3', 3' prolyl) that is also known as Actinomycin D or C₁. The Azetomicin and Dactinomycin molecules are identical, with the exception of the 3+ amino acid position on the peptides, wherein the 3' positions, in the case of Dactinomycin are both prolyl; in the case of the Azetomicin I are prolyl and azetidine-2-carboxyl; and in the case of Azetomicin II are both azetidine-2-carboxyl.

The summary results of this test on mice implanted with P388 leukemia are set forth in Table I:

TABLE I

| P 388 LEUKEMIA: QD AT DAYS 1-9 TREATMENT | | | | |
|---|---|---|---|---|
| DRUG | Mg/ Kg/ Inj. | SURVIVAL TIME MEDIAN (RANGE) | % ILS* | 60 DAY "CURES" |
| CONTROLS | 0 | 10 DAYS (7-15) | — | 0 |
| DACTINOMY-CIN | 0.1 | 21.5 (8-40) | 115 | 12% |
|  | 0.05 | 28 (13-39) | 180 | 0 |
| AZETOMICIN-II | 0.1 | 23 (6-39) | 130 | 12% |
|  | 0.05 | 22.5 (15-28) | 125 | 0 |
| AZETOMICIN-I | 0.2 | 60+ (24-48) | 500+ | 60% |
|  | 0.1 | 25.5 (21-38) | 155 | 0 |
|  | 0.05 | 25 (19-33) | 150 | 0 |

| ADVANCED P 388 LEUKEMIA: Q4Dx3 AT DAYS 5, 9, 13 TREATMENT | | | | |
|---|---|---|---|---|
| CONTROLS | 0 | 10 DAYS (7-16) | — | 0 |
| DACTINOMY-CIN | 0.15 | 19.5 (11-29) | 95 | 0 |
| AZETOMICIN-II | 0.6 | 25 (21-33) | 150 | 0 |
| AZETOMICIN-I | 0.6 | 37 (25-55) | 270 | 0 |

*ILS = increased life span.

From Table I, Azetomicin II is seen to be roughly comparable in activity to Dactinomycin, but Azetomicin I has clearly greater activity than both.

A sample of Azetomicin I was tested on mice infected with advanced Ridgeway osteogenic sarcoma. Of ten animals treated on a 12th day only injection schedule, complete regression was noted in all ten animals. These results have been compared with the results obtained in treating Ridgeway osteogenic sarcoma implanted mice with a number of clinically accepted anticancer drugs. Data supplied by Dr. F. Schabel and his coworkers at Southern Research Institute has been collected in Table II below, with the results from Azetomicin I testing also noted:

TABLE II

| DRUG-INDUCED REGRESSION OF ADVANCED RIDGEWAY OSTEOGENIC SARCOMA | | | |
|---|---|---|---|
| ANTICANCER DRUG* | (DAYS) SCHEDULE | REGRESSION (Number/Total) 50+%-PARTIAL / COM-PLETE | "CURES" (Number/Total) |
| ADRIAMYCIN | 12 | 7/8  7/8 | 0/8 |
| CYCLOPHOSPHAMIDE | 12 | 8/8  8/8 | 3/8 |
| L-SARCOLYSIN | 12 | 8/8  7/8 | 4/8 |
| BCNU | 12 | 0/8  0/8 | 0/8 |
| CCNU | 12 | 0/8  0/8 | 0/8 |
| DTIC | 12 | 0/10  0/10 | 0/10 |
| MITOMYCIN-C | 12 | 0/10  0/10 | 0/10 |
| CHLORAMBUCIL | 12 | 0/10  0/10 | 0/10 |
| THIO-TEPA | 12 | 0/10  0/10 | 0/10 |
| L-ASPARAGINASE | 12 | 0/10  0/10 | 0/10 |
| MITHRAMYCIN | 12 | 0/7  0/7 | 0/7 |
| BCG | 12 | 1/10  0/10 | 0/10 |
| VINCRISTINE | 12,16,20 | 10/10  8/10 | 0/10 |
| ARA-C | 12,12,20(q3h) | 7/10  3/10 | 0/10 |
| PREDNISONE | 12,16,20 | 0/10  0/10 | 0/10 |
| METHOTREXATE | 12,16,20,24 | 0/10  0/10 | 0/10 |
| AZACYTIDINE | 12,16,20,24 | 0/7  0/7 | 0/7 |
| FLUOROURACIL | 12,16,20,24 | 8/10  5/10 | 0/10 |
| MERCAPTOPURINE | 12-22 | 9/10  6/10 | 0/10 |
| DAUNOMYCIN | 12-17 | 9/12  3/12 | 0/12 |
| PROCARBAZINE | 12-20 | 0/10  0/10 | 0/10 |
| AZETOMICIN-I | 12 | 10/10  10/10 | 10/10 |

*All are clinically accepted anticancer drugs except AZETOMICINS

In another test, both Azetomicin I and Azetomicin II, were injected once into chicks infected with Rous sarcoma virus. The development of visible tumors was decreased by over 80% as compared with untreated or saline injected controls.

In a further test involving a cross section of gram-positive and gram-negative bacteria, Azetomicin I proved to be 70% as active as, but substantially less toxic/mg. than, Actinomycin D, and Azetomicin II proved to be 50% as active, and substantially less toxic/mg., against the growth of *Bacillus subtilis, Staphylococcus aureus* and *Staphylococcus albus.*

What is claimed is:

1. A biologically active compound having the formula:

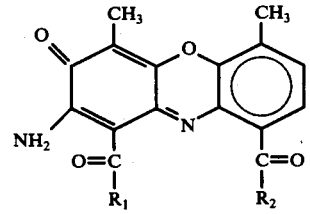

wherein R₁ and R₂ are five membered peptide lactones with the first peptide member counting from the multiple-ringed structure derived from threonine and the fifth peptide member derived from methyl-valine or methyl-isoleucine and with the lactone linkage extending from the first to the fifth member on each said peptide and wherein the third member of at least one of said peptides is selected from the group consisting of an azetidine-2-carbonyl moiety.

2. The compound of claim 1 wherein the third member of each said peptide is an azetidine-2-carbonyl moiety.

3. The compound:

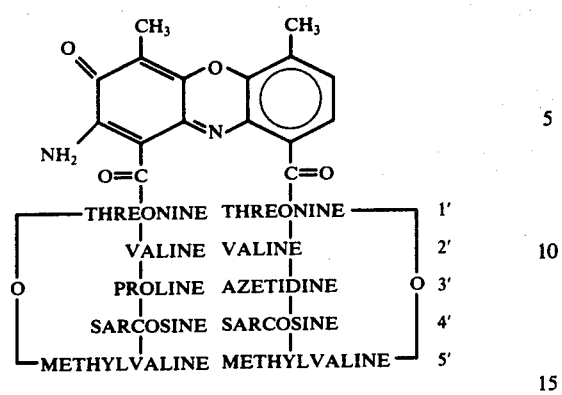
4. The compound of claim 3, wherein the azetidine and proline are interchanged.
5. The molecule, Azetomicin I.
6. The molecule, Azetomicin II.
* * * * *

Page 1 of 3

UNITED STATES PATENT OFFICE
CERTIFICATE OF CORRECTION

Patent No. 4,053,460      Dated October 11, 1977

Inventor(s) Martin A. Apple et.al.

It is certified that error appears in the above-identified patent and that said Letters Patent are hereby corrected as shown below:

Column 5, line 1-29, the structural formula:

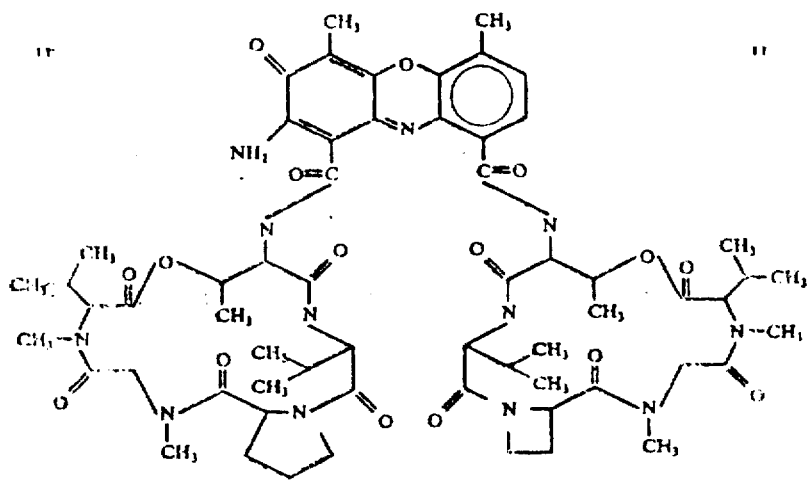

should read:

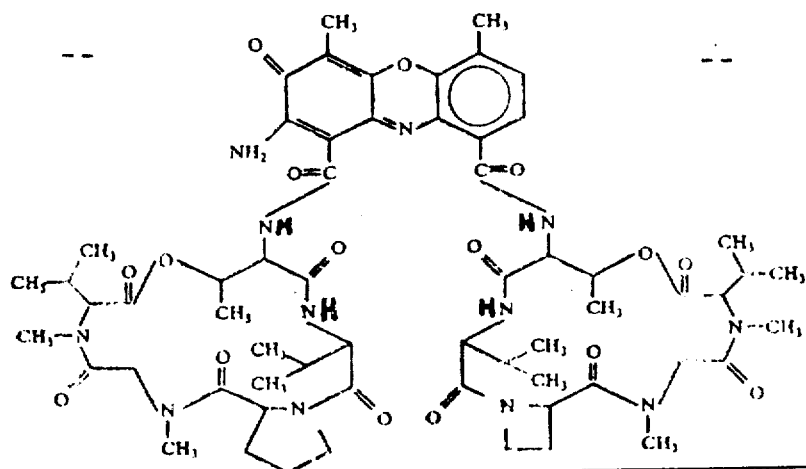

UNITED STATES PATENT OFFICE
CERTIFICATE OF CORRECTION

Patent No. 4,053,460                    Dated October 11, 1977

Inventor(s) Martin A. Apple et al.

It is certified that error appears in the above-identified patent and that said Letters Patent are hereby corrected as shown below:

Column 5, lines 60-65, the structural formula:

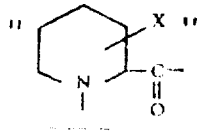   should read --   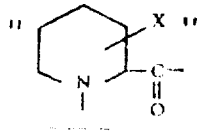   --

Column 6, line 39-41, the sentence should read:
--The 2' amino acids, that are most usually
D-valine, may be allo-isoleucine on either
one or both peptide chains.--

Column 6, line 41, "chromaphore" should be
--chromophore--.

Column 8, line    "Testing" should read
--Activity--.

Column 8, line 49, and column 9, lines 60-61, "infected" should read
--afflicted--.

Column 9, lines 61 and 65, and in Table II, "Ridgeway" should be spelled
--Ridgway--.

UNITED STATES PATENT OFFICE
CERTIFICATE OF CORRECTION

Patent No. 4,053,460              Dated October 11, 1977

Inventor(s) Martin A. Apple, et al

It is certified that error appears in the above-identified patent and that said Letters Patent are hereby corrected as shown below:

Column 9, line 29, "3+" should read --3'--.

Signed and Sealed this

Ninth Day of May 1978

[SEAL]

Attest:

RUTH C. MASON
Attesting Officer

LUTRELLE F. PARKER
Acting Commissioner of Patents and Trademarks